(12) United States Patent
Savage et al.

(10) Patent No.: US 12,168,779 B2
(45) Date of Patent: Dec. 17, 2024

(54) APPARATUS AND METHOD FOR CELL KILL CONFIRMATION

(71) Applicant: ABS Global, Inc., DeForest, WI (US)

(72) Inventors: Frederick Savage, DeForest, WI (US); David Appleyard, DeForest, WI (US); Zheng Xia, DeForest, WI (US); Matthew D. Ebersole, DeForest, WI (US); Daniel McAda, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 0 days.

(21) Appl. No.: 18/352,593

(22) Filed: Jul. 14, 2023

(65) Prior Publication Data
US 2023/0365924 A1    Nov. 16, 2023

Related U.S. Application Data

(63) Continuation of application No. 17/812,369, filed on Jul. 13, 2022, now Pat. No. 11,753,620, which is a
(Continued)

(51) Int. Cl.
*G01N 15/14* (2024.01)
*C12N 5/00* (2006.01)
(Continued)

(52) U.S. Cl.
CPC ......... *C12N 5/0093* (2013.01); *G01N 15/147* (2013.01); *G01N 21/6456* (2013.01); *G02B 21/16* (2013.01); *G01N 2021/646* (2013.01)

(58) Field of Classification Search
CPC ............... C12N 5/0093; G01N 15/147; G01N 21/6456; G01N 2021/646; G01N 15/149;
(Continued)

(56) References Cited

U.S. PATENT DOCUMENTS

| 5,135,759 A | 8/1992 | Johnson |
| 5,700,692 A | 12/1997 | Sweet |

(Continued)

FOREIGN PATENT DOCUMENTS

| WO | 9800943 A1 | 1/1998 |
| WO | 0219594 A2 | 3/2002 |

OTHER PUBLICATIONS

Premium Genetics (UK) LTD, PCT/GB2018/052633 filed Sep. 14, 2018, "The International Search Report and the Written Opinion of the International Searching Authority, or the Declaration", 13 pages, mailed Mar. 1, 2019.
(Continued)

*Primary Examiner* — Kiho Kim
(74) *Attorney, Agent, or Firm* — McKee, Voorhees & Sease, PLC

(57) ABSTRACT

A method and related apparatus for confirming whether a kill laser successfully destroys an undesired population of cells includes introducing fluorescent dye into cells, exciting the cells with a detection laser or a light emitting diode to cause the cell to fluoresce for a first time, measuring the amount of fluorescence in the cells with a detector capable of emitting a detection pulse, classifying the cells via embedded processing as undesired or desired cells based on the amount of fluorescence, firing a kill beam with a kill laser at any undesired cells, measuring the amount of fluorescence in the cells a second time to determine whether a fluorescent event was generated from the kill beam striking the cells, and providing feedback to an operator of the kill laser as to whether any fluorescent events were generated from the kill beam striking the cells.

16 Claims, 7 Drawing Sheets

Related U.S. Application Data continuation of application No. 16/442,058, filed on Jun. 14, 2019, now Pat. No. 11,427,804.

(60) Provisional application No. 62/685,614, filed on Jun. 15, 2018.

(51) Int. Cl.
  *G01N 21/64* (2006.01)
  *G02B 21/16* (2006.01)

(58) Field of Classification Search
  CPC ....... G01N 15/1459; G01N 2015/1006; G01N 15/14; G02B 21/16
  See application file for complete search history.

(56) References Cited

U.S. PATENT DOCUMENTS

| | | |
|---|---|---|
| 5,953,690 A | 9/1999 | Lemon et al. |
| 6,143,535 A | 11/2000 | Palsson |
| 8,941,062 B2 | 1/2015 | Wagner et al. |
| 10,333,018 B2 | 6/2019 | Savage et al. |
| 2005/0112541 A1 | 5/2005 | Durack et al. |
| 2008/0153087 A1* | 6/2008 | Frontin-Rollet ... G01N 33/5005 435/325 |
| 2011/0089340 A1 | 4/2011 | Merchez et al. |
| 2012/0038914 A1 | 2/2012 | Luscher |
| 2012/0225475 A1 | 9/2012 | Wagner et al. |
| 2012/0307244 A1 | 12/2012 | Sharpe et al. |
| 2014/0309782 A1 | 10/2014 | Sharpe et al. |
| 2016/0091410 A1 | 3/2016 | Krug |
| 2016/0370278 A1 | 12/2016 | Muir |
| 2017/0284940 A1 | 10/2017 | Butte et al. |
| 2018/0038783 A1 | 2/2018 | Yamamoto et al. |

OTHER PUBLICATIONS

"Luminex 200™ System User Manual" Luminex Corporation, 60 pages, revised Jul. 2005.

* cited by examiner

Kill Acquisition Electronics
Option 1 Diagram

Kill Confirmation Using one Detector

APPARATUS AND METHOD FOR CELL KILL CONFIRMATION

CROSS REFERENCE TO RELATED APPLICATION

This is a continuation patent application which claims priority under 35 U.S.C. § 120 to U.S. Ser. No. 17/812,369, filed Jul. 13, 2022, which claimed priority to U.S. Ser. No. 16/442,058, filed Jun. 14, 2019, now issued U.S. Pat. No. 11,427,804, which claimed priority under 35 U.S.C. § 119 to provisional patent application U.S. Ser. No. 62/685,614, filed Jun. 15, 2018. These patent applications are herein incorporated by reference in their entireties, including without limitation, the specification, claims, and abstract, as well as any figures, tables, appendices, or drawings thereof.

FIELD OF THE INVENTION

The present disclosure relates generally to an optical signal measurement method and apparatus for fluorescence signal confirmation in biotechnology. More particularly, the present disclosure relates to an apparatus and method for confirming whether a kill laser operating in the same, nearly the same, or different wavelength as a detection pulse and using high intensity ultraviolet irradiation successfully destroys an undesired population of sexed cells by measuring for an abrupt energy pulse created during a kill through the use of one or more luminescent dyes.

BACKGROUND OF THE INVENTION

Sexed semen (i.e., semen samples wherein the intact, fertile sperm cells are predominantly either X-chromosome bearing or Y-chromosome bearing) is important in a number of applications and industries. High purity sperm cell populations that have been differentiated based on chromosomal differences—such as, for example, sperm cell populations that are skewed toward X-chromosome bearing or Y-chromosome bearing populations of spermatozoa, rather than the naturally-occurring 50:50 X:Y chromosome split—can be utilized to accomplish in vitro or in vivo fertilization, including artificial insemination (AI) or in vitro fertilization (IVF) of ova or oocytes of numerous mammals such as bovids, equids, ovids, goats, swine, dogs, cats, camels, elephants, oxen, buffalo, or the like. See, e.g., U.S. Pat. No. 5,135,759.

The most common method for sexing sperm cells is to discriminate based on DNA content. In this context, sperm is combined with an extender and a luminescent dye to stain the DNA inside the sperm cell. The stained sperm cells are then placed in a sample fluid which is introduced into a channel of a microfluidic chip that uses focusing techniques to orient the sperm cell into a substantially single-file stream. After being properly oriented, the sperm cells are illuminated with a light source (e.g., a laser), which excites the luminescent dye in the DNA, giving off a fluorescent luminescence which is detected by a detector (e.g., a photo multiplier tube ("PMT"), an avalanche photodiode (APD), or a silicon photomultiplier (SiPM)). A sperm containing the X chromosome has more DNA than a Y chromosome-bearing sperm, resulting in the X chromosome-bearing sperm producing more luminescence in response to the detection light source. The detected luminescence is monitored and the system takes selective action, e.g., sorting or killing non-selected sexed sperm with a kill laser, on the individual sperm cells to achieve an end product with the desired characteristics, e.g., a sample with high concentration of either X or Y chromosome-bearing sperm. For example, if female calves are desired (e.g., for dairy production), then the system is calibrated to collect cells having detected luminescence parameters that are what would be expected of an X chromosome-bearing sperm cell. Alternatively, if male calves are desired (e.g., for beef production), then the system is calibrated to collect cells having detected luminescence parameters that are what would be expected of a Y chromosome-bearing sperm cell.

Sperm cells may also be distinguished based on DNA content by other methods that do not utilize a DNA dye. For example, U.S. Pat. No. 8,941,062 describes systems and methods of cytometry involving presenting a single sperm cell to at least one laser source configured to deliver light to the sperm cell in order to induce bond vibrations in the sperm cell DNA and detecting the signature of the bond vibrations. Sperm cells may also be analyzed and distinguished based on the presence or absence of cell surface markers or protein, through binding of a fluorescently labeled ligand, such as an antibody. Other methods for discriminating sperm cells may utilize other features of sperm cells, such as mass or volume, to differentiate between those that contain X-chromosomes and those that contain Y-chromosomes. These discrimination and detection methods similarly permit the cells to be selectively differentiated and for the sample to be sexed.

Sexing techniques include a variety of methods to sort, separate, eliminate, destroy, or inactivate unwanted cells. For example, so-called laser kill methods involve exposure of particular cells to a laser with sufficient energy to inactivate the cells. Cells may also be separated into populations through sorting, for example through droplet formation and deflection as described in U.S. Pat. No. 5,700,692.

In cell discrimination techniques, including sperm cell sexing applications, proper orientation, spacing, and location of the cells within the microfluidic system is essential to effective operation. For example, positioning and orientation are both essential being able to effectively detect the difference in fluorescence of X- and Y-chromosome bearing sperm cells stained with a DNA-intercalating dye, as both the positioning of cells within the beam of the detection laser and the orientation of the cells with respect to the detector significantly impact the amount of fluorescence detected. Alterations in the fluorescence in turn directly affect the ability to distinguish differences in the fluorescence signal between X-chromosome and Y-chromosome bearing cells.

Semen sexing instruments are typically cytometers used to sex semen by measuring DNA content of a stained bull semen sample. Once the desired population (e.g. male or female cells) is identified by the system, the instrument is able to obtain gender skew through the use of a kill laser. The kill laser strikes and destroys the undesired population of sexed cells on an individual basis through an abrupt energy pulse which disrupts the membrane of the cells, thereby causing the sexed cells to become infertile.

Sexed semen systems known in the art run with an initial kill beam alignment in which operators manually adjust the beam position and observe cells under a microscope to determine if the instrument is achieving an adequate kill. These are open loop control systems, and once alignment is achieved it is no longer tracked throughout the run.

Prior methods for checking the purity percentage of a population of sexed cells after the use of a semen sexing instrument were accomplished manually by operators and via sampling of outputs. Essentially, dead cells were measured on a microscope slide off instrument (i.e. a "kill count"

was manually taken after use of the semen sexing instrument). The manual kill count is labor intensive and requires additional consumables and lab space.

Other sexed semen machines are known in the art which do not utilize a kill laser. For example, in "droplet in air" sexed semen systems, sperm cells pass through a sorting machine in drops of liquid containing a single sperm cell per droplet after a fluorescent dye is incorporated into the DNA of the sperm cells. The machine detects the amount of florescence each cell emits. Because female (X-chromosome bearing) sperm cells are heavier than male (Y-chromosome bearing) sperm cells an X sperm cell will have more florescence than an Y sperm cell. A positive or negative charge is applied to the droplet depending on the type of sperm cell in it. Then, the machine can sort them into different collection tubes, based on the charge on the droplet, as it moves through a magnetic field. These droplet in air sexed semen systems are also open loop control systems, and there is no feedback mechanism for sort confirmation.

Thus, there exists a need in the art for an apparatus and method for measuring a kill pulse (i.e. confirming the kill beam has struck a cell) within sexed semen systems utilizing a kill laser and for an apparatus and method for providing sexed semen systems which are automated, conducted in real time, and give closed loop feedback to the system.

BRIEF SUMMARY OF THE INVENTION

Therefore, it is a primary object, feature, or advantage of the invention to improve on or overcome the deficiencies in the art.

It is another object, feature, or advantage of the invention to provide a sexed semen apparatus which produces a consistently higher purity product.

It is another object, feature, or advantage of the invention to provide a sexed semen apparatus which verifies kill laser alignment is consistent throughout a run.

It is another object, feature, or advantage of the invention to provide a sexed semen apparatus which overcomes the drawbacks of an open loop system, such as kill beam alignment which drifts over time during long runtimes and bull changes.

It is still yet a further object, feature, or advantage of the invention to destroy or reduce manual examination of cells under a microscope during alignment by automating the confirmation process.

It is still yet a further object, feature, or advantage of the invention to provide a sexed semen apparatus wherein the detection and kill laser use the same wavelength and allow for gender detection and kill confirmation using only one dye.

It is still yet a further object, feature, or advantage of the invention to provide a sexed semen apparatus wherein the kill laser uses ultraviolet or infrared irradiation to successfully destroy an undesired population of sexed cells.

It is still yet a further object, feature, or advantage of the invention to provide a sexed semen apparatus which measures absorbance instead of fluorescence.

It is still yet a further object, feature, or advantage of the invention to provide a sexed semen apparatus that detects the loss of signal or excitation power.

It is still yet a further object, feature, or advantage of the invention to provide a sexed semen apparatus that is usable for a wide variety of applications.

It is still yet a further object, feature, or advantage of the invention to provide a sexed semen apparatus that is safe to operate.

It is still yet a further object, feature, or advantage of the invention to a sexed semen apparatus that is cost effective.

It is still yet a further object, feature, or advantage of the invention to provide a sexed semen apparatus that provides repeatable and consistent performance among different instruments and samples for processing.

It is still yet a further object, feature, or advantage of the invention to provide a sexed semen apparatus that is reliable and durable.

It is still yet a further object, feature, or advantage of the invention to provide a sexed semen apparatus that can be easily manufactured, installed, repaired, and disassembled.

It is still yet a further object, feature, or advantage of the invention to provide a sexed semen apparatus that is aesthetically pleasing.

According to some aspects of the disclosure, a method which provides real time closed-loop feedback for a system that destroys an undesired cell includes detecting a first fluorescence of a cell with a detector, classifying the cell as an undesired cell or a desired cell based on the detection of the first fluorescence, eliminating the undesired cell if the cell is classified as an undesired cell, and confirming, in real time, whether the undesired cell was destroyed by detecting a second fluorescence of the cell.

According to additional aspects of the disclosure, the method may also include introducing cell dye into the cell.

According to additional aspects of the disclosure, the method may also include exciting the cell with a detection laser or a light emitting diode to cause the first fluorescence.

According to additional aspects of the disclosure, the method may also include aligning the detection laser and the detection laser may utilize beam conditioning to aid in achieving a correct spot size at the cell.

According to additional aspects of the disclosure, the method may also include collecting the cell if the cell is classified as a desired cell.

According to additional aspects of the disclosure, the method may also include aligning the kill laser.

According to additional aspects of the disclosure, the method may also include queuing a kill laser to destroy the undesired cell by producing a charge signal which delays eliminating the cell.

According to additional aspects of the disclosure, the method may also include firing a kill beam with the kill laser to destroy the undesired cell.

According to additional aspects of the disclosure, the kill laser may operate in the same excitation wavelength as a detection pulse emitted by the detector.

According to additional aspects of the disclosure, the method may also include creating a sample flow by allowing a sheath fluid to enter a semen sexing instrument and wherein the cell is excited within the sample flow.

According to additional aspects of the disclosure, the first fluorescence of the cell may be determined the sex of the cell.

According to additional aspects of the disclosure, detecting the second fluorescence may be accomplished with the same detector or a different detector.

According to additional aspects of the disclosure, the method may also include storing an output related to whether the undesired cell was destroyed.

According to additional aspects of the disclosure, the method may also include repeating the detecting, classifying, destroying, confirming, and storing steps and calculating a purity percentage associated with a population of cells.

According to other aspects of the disclosure, a sexed semen system includes a detection laser capable of exciting a sperm cell, a first fluorescence detector, a computer processing unit for determining the sex of the sperm cell based on an output of the first fluorescence detector, a kill laser, a second fluorescence detector, and real time, closed-loop feedback confirming whether undesired sperm cells are destroyed by the kill laser based on an output from the second fluorescence detector.

According to additional aspects of the disclosure, the sexed semen system further includes a sheath fluid encapsulating the sperm cell.

According to additional aspects of the disclosure, the sexed semen system may utilize inertial flow focusing.

According to additional aspects of the disclosure, the sexed semen system further includes a first detection laser lens assembly.

According to additional aspects of the disclosure, the sexed semen system further includes a second detection laser lens assembly.

According to additional aspects of the disclosure, the sexed semen system further includes a first kill laser lens assembly.

According to additional aspects of the disclosure, the sexed semen system further includes a second kill laser lens assembly.

According to additional aspects of the disclosure, the first fluorescence detector and the second fluorescence detector may be avalanche photodiode (APD) sensors or silicon photomultiplier sensors (SiPM).

According to additional aspects of the disclosure, the sexed semen system further includes kill acquisition electronics including at least a wide band transimpedance amplifier operatively connected to the second detector and readout circuitry.

According to additional aspects of the disclosure, the kill acquisition electronics may further comprise a secondary amplifier.

According to additional aspects of the disclosure, the kill acquisition electronics may further comprise a high-speed comparator.

According to additional aspects of the disclosure, the sexed semen system further includes a USB to serial converter or an analog signal input that allows a voltage at the second detector to be adjusted and a high voltage custom power bias supply which generates the voltage at the second fluorescence detector.

According to additional aspects of the disclosure, the sexed semen system further includes digital circuitry which reads a digital code associated with the output of the first fluorescence detector, said digital circuitry comprising a field programmable gate array, a decoder, flip flops, or a digital signal processor chip.

According to additional aspects of the disclosure, the kill acquisition electronics may comprise a correlated double sampler.

According to additional aspects of the disclosure, the correlated double sampler may initially trigger a first value from a charge signal from the kill laser.

According to additional aspects of the disclosure, the sexed semen system further includes a high-speed analog to digital converter.

According to other aspects of the disclosure, a sexed semen system includes a detection laser capable of exciting a sperm cell, a fluorescence detector, a computer processing unit for determining the sex of the sperm cell based on an output of the fluorescence detector, a kill laser, and real time, closed-loop feedback confirming whether undesired sperm cells are destroyed by the kill laser based on an output from the fluorescence detector.

According to additional aspects of the disclosure, the sexed semen system further includes a first detection laser lens assembly.

According to additional aspects of the disclosure, the sexed semen system further includes a kill laser lens assembly.

According to additional aspects of the disclosure, the sexed semen system further includes a second detection laser lens assembly.

According to additional aspects of the disclosure, the sexed semen system further includes kill acquisition electronics including at least a wide band transimpedance amplifier operatively connected to the fluorescence detector and readout circuitry.

According to additional aspects of the disclosure, the kill acquisition electronics may further comprise a secondary amplifier.

According to additional aspects of the disclosure, the sexed semen system further includes further comprising a high-speed analog to digital converter.

According to additional aspects of the disclosure, the sexed semen system further includes kill acquisition electronics including an analog signal split operatively connected to the fluorescence detector and readout circuitry, wherein the analog signal split is accomplished using a low bandwidth transimpedance amplifier, a secondary amplifier, a high bandwidth transimpedance amplifier, and a combination secondary amplifier and high pass filter.

These or other objects, features, and advantages of the invention will be apparent to those skilled in the art. The invention is not to be limited to or by these objects, features and advantages. No single embodiment need provide each and every object, feature, or advantage.

Figure 1:
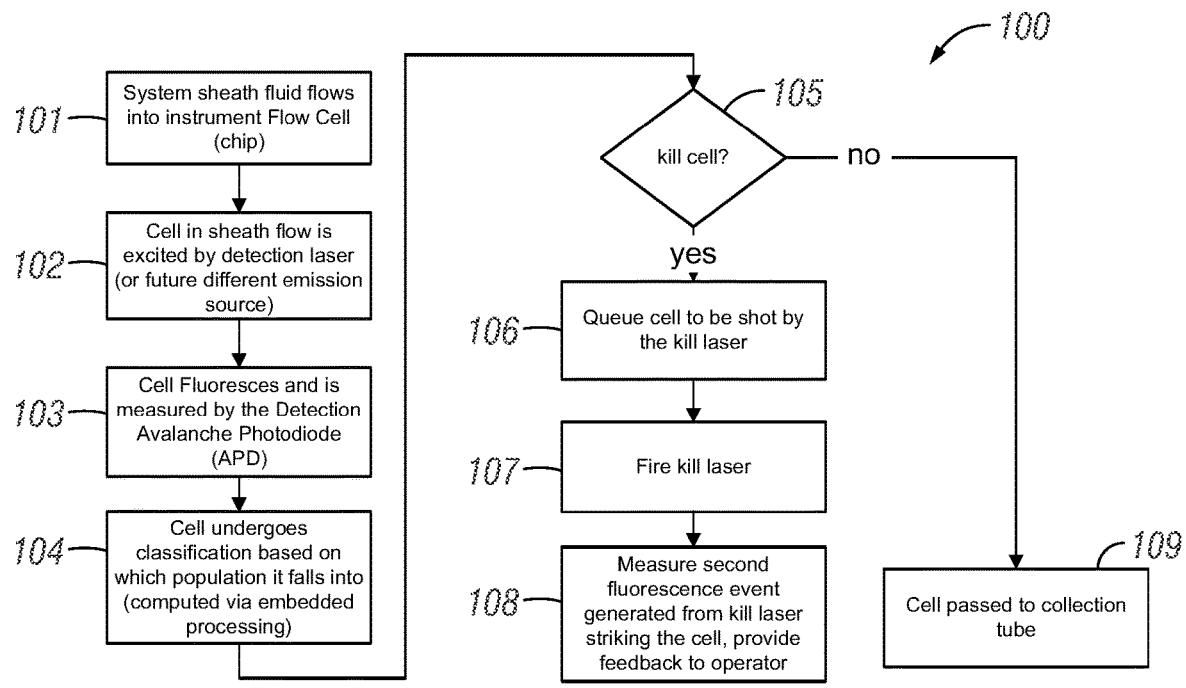
FIG. 1 shows an illustrative high-level diagram of a cell process for a sexed cell instrument according to some aspects of the present disclosure.

Various embodiments of the invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION

The following definitions and introductory matters are provided to facilitate an understanding of the present invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

Reference is made to the accompanying drawings which form a part hereof, and in which is shown by way of illustration specific embodiments in which the invention may be practiced. These embodiments of the invention will be described in detail with reference to the drawings, wherein like reference numerals represent like parts throughout the several views. These embodiments are described in sufficient detail to enable those skilled in the art to practice the invention and it is to be understood that other embodiments may be utilized. Mechanical, procedural, and other changes may be made without departing from the spirit and scope of the invention. The following detailed description is, therefore, not to be taken in a limiting sense, and the scope of the invention is defined only by the appended claims, along with the full scope of equivalents to which such claims are entitled.

As used herein, the terminology such as first, second, vertical, horizontal, top, bottom, upper, lower, front, rear, end, sides, concave, convex, and the like, are referenced according to the views presented. It should be understood, however, that the terms are used only for purposes of description and are not intended to be used as limitations. Accordingly, orientation of an object or a combination of objects may change without departing from the scope of the invention.

For the purposes of the present disclosure, the term "Stokes shift" is defined as the difference (in wavelength or frequency units) between positions of the band maxima of the absorption and emission spectra, as is commonly understood in the art. The term "destroy" as used herein refers to rendering something useless (e.g. a cell) for its intended purpose. The definitions of other technical terms will become apparent from their usage in the present disclosure.

According to a non-limiting example of the present disclosure, FIG. 1 shows an illustrative high-level diagram of a method for confirming whether a kill laser successfully destroys an undesired population of cells 20, and more particularly, a cell process for a sexed semen system.

The method 100 begins with or right after introducing cell dye, such as Hoescht 33342, into a cell (i.e. staining the cell). Hoescht 33342 is excited by ultraviolet (UV) light at approximately 350 nanometers and emits blue-cyan fluorescent light around an emission spectrum maximum at 461 nanometers. Hoescht 33258 (magenta) may also be used by the sexed semen system due to having similar excitation/emission spectra as Hoescht 33342. Unbound dye has its maximum fluorescence emission in the 510-540 nanometer range. Hoechst stains can be excited with a xenon- or mercury-arc lamp or with an ultraviolet laser. There is a considerable Stokes shift of the same electronic transition between the excitation and emission spectra that makes Hoechst dyes useful in experiments in which multiple fluorophores are used. The fluorescence intensity of Hoechst dyes increases with the pH of the solvent.

Hoechst dyes are soluble in water and in organic solvents such as dimethyl formamide or dimethyl sulfoxide. Concentrations can be achieved of up to 10 mg/mL. Aqueous solutions are stable at 2-6° C. for at least six months when protected from light. For long-term storage the solutions are instead frozen at ≤−20° C.

The dyes bind to the minor groove of double-stranded DNA with a preference for sequences rich in adenine and thymine. Although the dyes can bind to all nucleic acids, AT-rich double-stranded DNA strands enhance fluorescence considerably. Hoechst dyes are cell-permeable and can bind to DNA in live or fixed cells. Thus, these stains are often called supravital, meaning that live cells survive a treatment with these compounds. Cells that express specific ATP-binding cassette transporter proteins can also actively transport these stains out of their cytoplasm.

In an exemplary embodiment, during the flowing step 101, a sheath fluid flows into a semen sexing instrument or cytometer to create a laminar sample flow, perform hydrodynamic focusing on the sample flow, and move cells through the system flow cell. Cells travel inside the flow cell from the detection spot to the kill spot.

A sample is introduced into a microfluidic chip as a sample flow. The sample flow is then acted upon to create a focused sample flow wherein the cells in the sample flow substantially all have the same orientation and positioning within the microfluidic channel as the cells reach the interrogation region and retain and as the cells reach the kill spot.

Alternative technology that does not use sheath fluid or hydrodynamic focusing such as inertial flow focusing may also be used. Thus, the present disclosure encompasses any method for focusing, orienting, aligning, and/or ordering the cells in a sample flow into a single or essentially single file line for detection and ablation.

During the exciting step 102, a cell within the sample flow is excited by a detection laser or a light emitting diode to cause the cell to fluoresce for a first time.

During the first measuring step 103, the amount of fluorescence in the cell is measured for a first time with a first detector, such as an avalanche photodiode (APD) sensor, a photomultiplier tube (PMT), or a silicon photomultiplier (SiPM) capable of emitting an electronic signal indicative of the detected fluorescence, hereinafter referred to as a detection pulse.

During the classifying step 104, the cell undergoes classification based on which population it falls into as a computer processing unit computes, via embedded processing, whether the measured amount of fluorescence in the cell fails to meet or exceeds a predetermined threshold. The predetermined threshold has some significance to identification of cells which fall into the undesired population.

For example, in the determining step 105, a sexed semen system uses a predetermined threshold of fluorescence which correlates to the total DNA content of each cell. Then, because differences in DNA (typically 3.8% in bovine sperm cells) and the corresponding difference in dye bound to the DNA cause the fluorescence emitted by a female sperm cell to be greater than the fluorescence emitted by a male sperm cell, the sexed semen system can determine which cells to destroy (e.g. all male cells) based on the fluorescence measured for each cell. If the cell is classified as an undesired cell, the sexed semen system queues a kill laser to fire a kill beam at the cell during the queuing step 106 and subsequently fires the kill beam during the firing step 107.

The kill laser exposes the cells determined to be undesirable to one of more pulses sufficient to destroy the targeted cell. Cells can be destroyed by the kill laser preferably by disrupting the cell membrane (e.g. slicing the cell) or separating part of the cell (i.e. the sperm cell tail). In some instances, exposure to the kill laser pulse does not disrupt the cell but does result in sufficient exposure to otherwise damage or incapacitate the cell, for example by inducing intracellular damage, such as DNA damage like cross-linking or DNA strand disruption. In such cases, the cell may not have observable defects upon microscopic inspection but may nevertheless be considered destroyed. According to certain aspects of the present invention, it is possible to differentiate between different modes of cellular destruction by determining the extent of laser exposure the cell has experienced. In further aspects, it is possible to determine if the cell was exposed to a laser pulse, but at a level insufficient to destroy the cell.

During the second measuring step and providing step 108, a fluorescence signal emitted by the cell is measured a second time, only upon effective exposure to a pulse from the kill laser. The dye bound to the DNA in each cell fluoresces upon exposure to the kill laser pulse, thereby allowing for a determination to be made as to whether a fluorescent event was generated from the kill beam striking the cell, and the sexed semen system provides feedback to an operator of the kill laser or to the system to permit automated re-alignment of the kill laser as to whether a fluorescent event was generated from the kill beam striking the cell. In some embodiments the sexed semen system may utilize a single detector and in other embodiments the sexed semen system may utilize two detectors. All cells, including cells classified as desired cells, unmolested cells, undesired cells, and ablated cells, are passed to a collection tube during the collection step 109. Optionally thereafter, a sorting process may take place to eliminate or remove any cells that were killed or should have been killed but were not confirmed. A contingency laser may be used to facilitate or improve the sorting process.

The present disclosure notes the desirability of a cell may depend on, but is not limited to, the sex of the cell, the size or cell surface characteristics of the cell, whether the cell has any chromosomal deficiencies which are known to cause disease, etc. It is also appreciated the stain, light emitted (fluorescence), and signal strength are proportionally related to one another and to the presence of the binding target for the dye/fluorescent tag.

In some aspects, confirming whether undesired cells were destroyed is performed on a cell-by-cell basis, wherein the fluorescent signal from individual cells is assessed to determine whether a sufficient exposure has occurred. In other aspects, confirming whether undesired cells were destroyed can be accomplished using population-level confirmation. In this approach, confirmation is accomplished by sampling a first set of cells (i.e. measuring the intensity of the fluorescence signal generated via exposure to the kill laser), adjusting one or more machine parameters (laser alignment, delay timing), taking new measurements for a second set, and comparing the measured values for the first and second sets.

Figure 2:
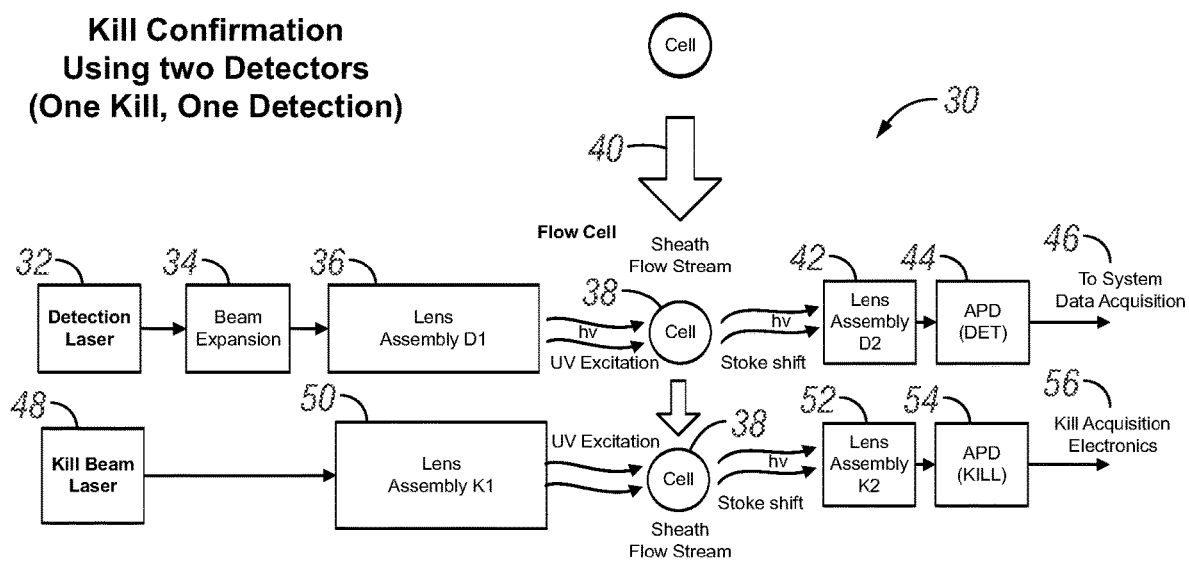
FIG. 2 shows a diagram of the sexed semen system implementation wherein a separate detection sensor (and APD or a SiPM) and kill sensor (APD or SiPM) are used in the instrument according to some aspects of the present disclosure.

According to a non-limiting example of the present disclosure, FIG. 2 shows a diagram of a two-detector kill confirmation system implementation which includes the components of an improved semen sexing instrument 30. The improved semen sexing instrument 30 has a detection laser or light emitting diode 32 used to excite the cell dye for DNA measurement. The detection laser 32 benefits by utilizing beam conditioning 34 and a first detection laser lens assembly 36 to achieve the correct spot size of a detection spot at the flow cell 38.

In a preferred embodiment, the detection laser 32 is a Vanguard 355/350 laser, which has become the current industry standard for semen evaluation. The Vanguard 355/350 laser is a state-of-the-art diode-pumped solid-state (DPSS) laser specifically designed to produce exceptionally reliable quasi-CW UV output. This Vanguard 355/350 laser uses advanced mode-locking technology to deliver 350 mW of picosecond pulses at 355 nanometers with low noise and excellent TEM00 mode quality. The Vanguard 355/350 laser features high stability beam characteristics and low cost of ownership necessary for a variety of OEM applications, plus the integration convenience of an air-cooled chassis. Designed for the stringent demands of semiconductor wafer processing, the Vanguard 355/350 is also ideal as a UV laser source for cell flow cytometry and micro-material processing applications. The Vanguard series of lasers are field proven with over 1,000 systems in a wide variety of operations. The system can be remotely controlled via RS 232 interface and incorporates extensive on-board data logging of key parameters. Closed-loop power control ensures consistent UV output power to less than 2% variation from specified level. Preventative maintenance adjustment of the THG crystal and Saturable Absorber Mirror (SAM) optimizes performance and extends the operational life of the Vanguard laser. The diode module is a design for exceptionally long life, and is located remotely in the power supply, enabling easy replacement without laser head alignment.

The Vanguard 355/350 laser may be "over" powered for a single station of detection. As such, the detection beam path may be split among several workstations. The height of the beam path is approximately 12-14 µm parallel to the direction of sperm travel and has a Gaussian distribution. The width of the beam path is approximately 100 µm perpendicular to the direction of sperm travel, has a Gaussian distribution, and provides a "plateau" of intensity covering core stream position.

Referring back to FIG. 2, a sample fluid containing cells enters the microfluidic channel in the microfluidic subsystem of the improved semen sexing instrument or cytometer 30 and moves cells through the system flow cell 38. As the sample flow stream 40 moves the cells, a detection laser lens assembly 42 steers a first detection pulse emitted by a detection laser 32 into the sample flow. The first detection pulse illuminates a cell within the sample flow, and the fluorescent dye bound the DNA of the cell produces a fluorescent emission event, which is directed onto a surface of the first detector 44. The first detector 44 is an avalanche photodiode (APD) or a silicon photomultiplier (SiPM) sensor and the optics for measuring the fluorescence signal from the cell during interrogation. The first detector 44 is the sensor used to classify male and female populations of cells and aids in determining which cells are undesirable. The measurement taken by the first detector 44 is sent to system data acquisition 46 of the improved semen sexing instrument or cytometer 30.

All cells then travel inside the flow cell 38 from the detection spot to a kill spot. A kill laser 48 of the improved semen sexing instrument or cytometer 30 is used to destroy undesirable cells. The kill laser 48 has a "high" energy at a short recharge time, a stable pulse to pulse consistency, and a pulse on demand operation. In a preferred embodiment, the kill laser 48 is a 355 nanometer Q-switch laser which leverages the dye in the cells and disrupts the membrane of the cells. Oversaturation/emission of the dye renders the cells infertile because ultraviolet (UV) light (e.g. 355 nanometers) is known to cause DNA damage. The present disclosure appreciates however that different wavelengths of a kill laser (e.g. infrared) would also kill sperm cells, but with a different mechanism.

A kill laser lens assembly 50 directs the kill beam (as shown in FIGS. 23 and 24) to the kill spot in the flow cell 38 and establishes the spot size. The shape of the kill beam is typically a knife blade shape. Additionally, the energy density of the kill beam, tight focusing of the cell stream, and alignment of the kill laser, are all critical factors to consider for proper operation of the sexed semen system.

In a preferred embodiment, the kill laser 48 and the first detection pulse have the same or substantially similar wavelengths. Operation of kill and detection at the same or substantially similar wavelengths allows for the use of a single cell stain (dye) because the stained DNA within the cell will fluoresce a second time. In other words, the cell undergoes two separate fluorescent events: a first event when illuminated by the detection laser; and a second event when struck by the kill beam. A second kill laser lens assembly 52 steers a second pulse emitted by the kill laser 48 into the sample flow where it interacts with a cell. The laser pulse is absorbed by the cell, resulting both in cell destruction, and fluorescence emission by the DNA dye. The emitted fluorescence is directed to the surface of the second detector 54. The second detector 54 is an avalanche photodiode (APD) sensor, photomultiplier tube (PMT), or a silicon photomultiplier (SiPM) and the optics for measuring the fluorescence signal generated from the kill beam striking the cell during the fluorescent event. Feedback can then be provided to an operator of the kill laser or to the system to facilitate automated re-alignment of the kill laser 48 as to whether a fluorescent event was generated from the kill beam striking the cell via kill acquisition electronics 56.

Figure 3:
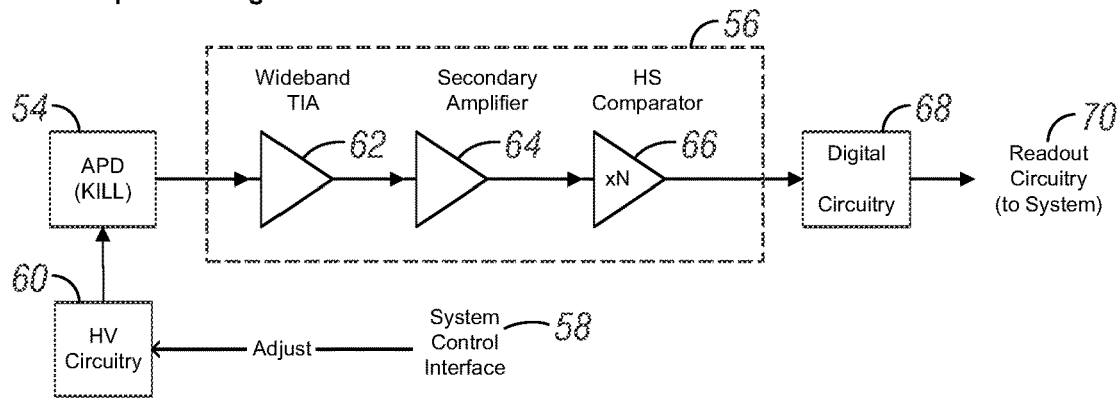
FIG. 3 shows a diagram of a first option for the kill acquisition electronics used in the sexed semen system of FIG. 2 for kill confirmation which includes a high-speed comparator according to some aspects of the present disclosure.

As shown in FIG. 3, the kill acquisition electronics 56 are operatively connected to the second detector 54 and readout circuitry 70. In certain aspects, the second detector 54 is biased using custom high voltage circuitry 60. The system control interface 58 allows the high voltage circuitry 60 to be dialed up or down to increase the optical signal gain of the detector.

The system control interface 58 is either a USB to serial converter or an analog signal input similar that allows the voltage at the sensor 54 to be adjusted. The voltage on the sensor 54 sets the optical signal gain and therefore adjusting this voltage allows for dynamic gain control of the optical signal. The system control interface 58 typically includes a microcontroller and any necessary peripherals such as analog circuit components to adjust the high voltage circuitry depending on the desired functionality.

The high voltage circuitry 60 is the high voltage custom power bias supply that generates the voltage at the sensor 54. The high voltage circuitry is adjustable through the system control interface 58 which allows the optical signal gain to be adjusted. In a preferred embodiment, the circuit maintains an optical gain factor (M) in the range of fifty to one hundred and remains static in the implementation.

The kill acquisition electronics 56 may comprise a wide band/low bandwidth transimpedance amplifier 62, a secondary amplifier 64, and a high-speed comparator 66.

The kill laser 48 creates a very short pulse of optical energy to destroy the cell. The fluorescence signal generated from the pulse is proportional to the half-life of the dye and time the kill laser is on. A pulse is created in the 10-15 nanosecond range and therefore requires a wide band transimpedance amplifier 62. The sensor 54 generates a current output, and the transimpedance amplifier 62 converts the narrow current pulse into a voltage pulse.

The secondary amplifier 64 is a voltage amplifier with a primary function of providing additional gain and maintaining signal bandwidth. Due to the short pulse measurement, the first stage amplifier may be unable to meet system gain bandwidth requirements without a secondary amplifier. Using the secondary amplifier 64 allows the signal bandwidth to be preserved and signal gain increased at the cost of adding additional components.

Because the kill beam fluorescence pulse is approximately 10-15 nanoseconds wide, a high-speed measurement is required. In the embodiment shown in FIG. 3, a high-speed comparator 66 is used to determine the pulse height rather than using an analog to digital converter. The high-speed comparator block can use any number (N) of high-speed comparators 66 to generate the pulse amplitude information, however the number of high-speed comparators 66 generally depends on the resolution desired for the pulse amplitude measurement. The pulse amplitude is measured by monitoring which comparators have tripped. Even a single comparator could be used for detecting a pulse height kill event. Multiple comparators however provide a much greater amount of information.

Figure 4:
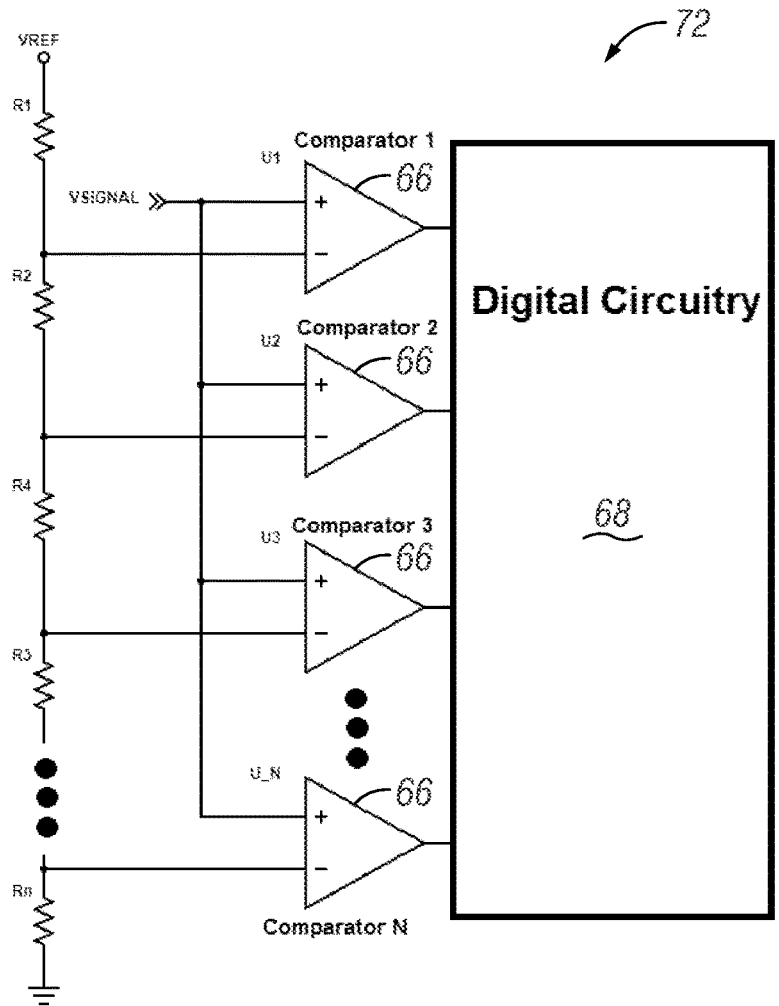
FIG. 4 shows a diagram of a comparator ladder configuration according to some aspects of the present disclosure.

The high-speed 66 comparators will be setup in a comparator/resistor ladder configuration 72 as shown in FIG. 4. The comparator ladder configuration 72 will convert the pulse into a digital code that can be read using digital electronics 68. The VREF input is controllable by the user. The purpose of the VREF input is to create a voltage the high-speed comparator 66 is measuring against, which is similar to flash analog to digital converter architecture. By allowing for an adjustable VREF, the circuit effectively allows for dynamic scaling and gain control for incoming pulses. VSIGNAL is the input voltage pulse generated from the sensor 54 to transimpedance amplifier 62 to voltage amplifier 64 signal chain.

The digital circuitry 68 may comprise a field programmable gate array (FPGA), a decoder, flip flops, or a digital signal processor chip. Once the pulse is converted into a digital value, the system will use one of these components to obtain the pulse data. In a preferred embodiment, the digital circuitry 68 is implemented with the use of an FPGA for design flexibility.

Figure 5:
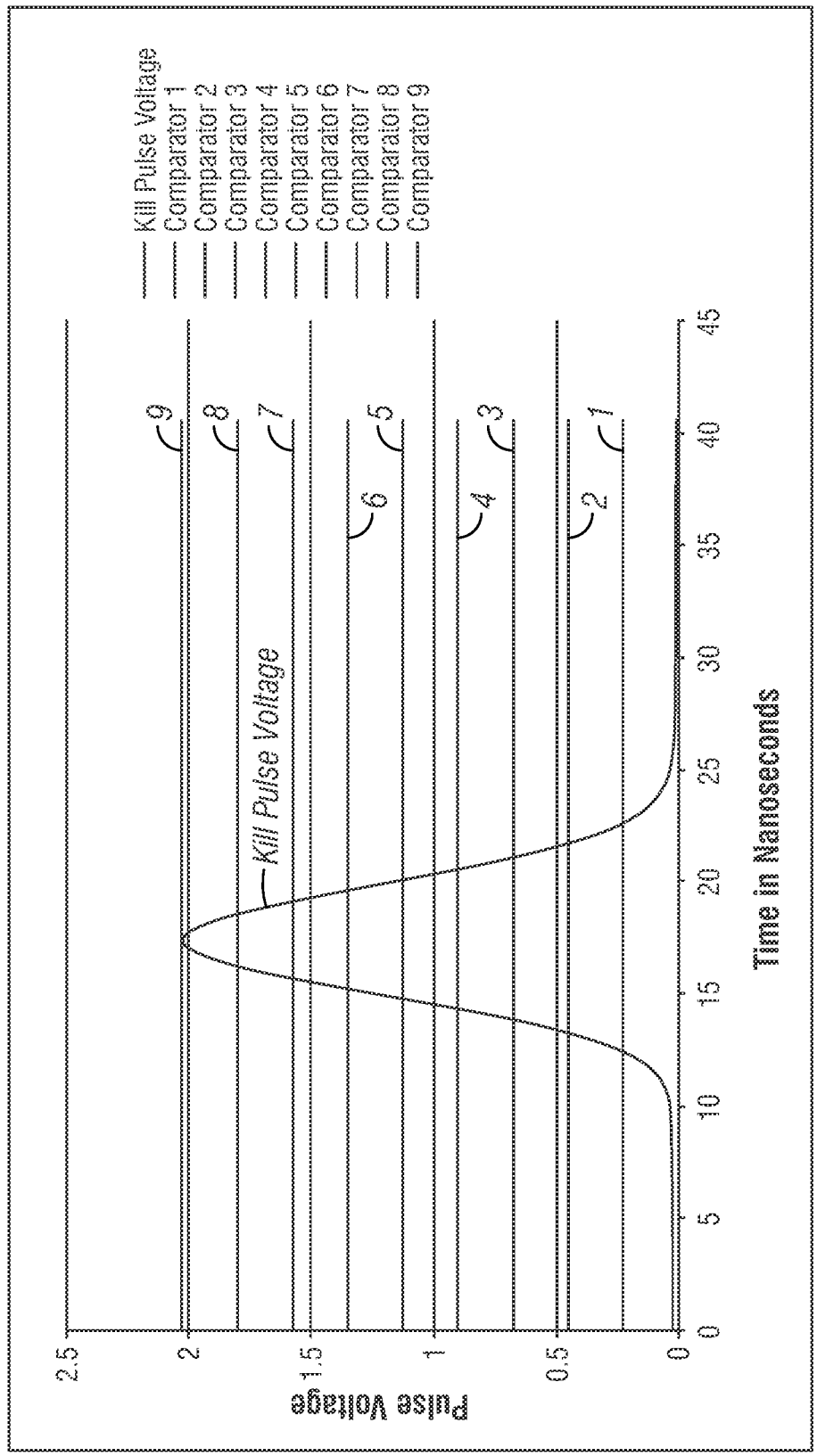
FIG. 5 shows a graphical representation of a high-speed comparator trip values according to some aspects of the present disclosure.

FIG. 5 demonstrates comparator trip values for a kill confirmation implementation according to aspects of the present disclosure. For example, the kill confirmation pulse has been received by the second sensor 54 and amplified to a 2V signal. The 2V pulse signal is sent to the comparator circuit 72. In the example shown, all comparators 66 trip except for comparator 9, which returns a digital value of 011111111. In the example shown, VREF is set to 2.025V and allows each comparator to measure amplitude in 0.225V step increments. Resolution is established by the following formula:

$$V\_STEP\_RESOLUTION=VREF/(N),$$

wherein N is the number of comparators 66 and VREF is the voltage input shown in FIG. 4. Allowing for a changing VREF enables the pulse measurement to be adjusted dynamically.

To measure a higher amplitude pulse, VREF simply needs to be adjusted up. To measure a smaller pulse with more resolution, VREF can be adjusted down. Whatever VREF is set to, the number of comparators N will create a new V_STEP_RESOLUTION for the digital code generated. Sixteen high-speed comparators 66 with an adjustable VREF may be preferred to satisfy several of the objects of the present disclosure set forth herein. High-speed comparators 66 must be selected that can measure the very short pulse duration near the peak of the pulse.

Figure 6:
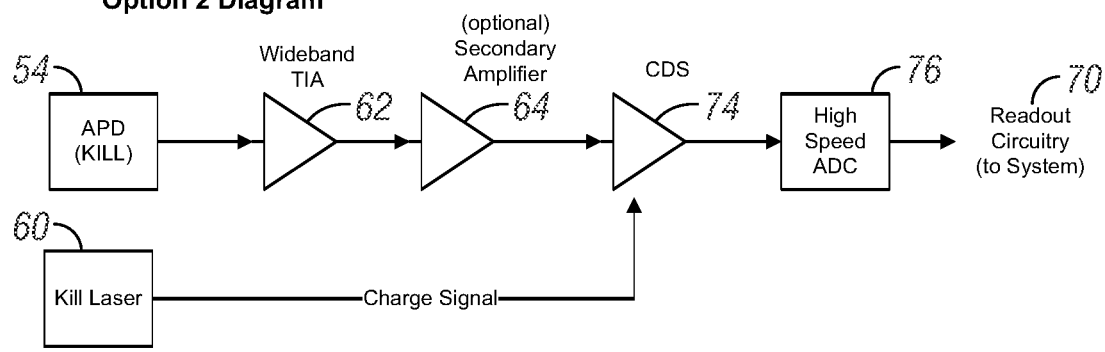
FIG. 6 shows a diagram of a second option for the kill acquisition electronics used in the sexed semen system of FIG. 2 for kill confirmation which includes a correlated double sampler according to some aspects of the present disclosure.

As shown in FIG. 6, another option for the kill beam confirmation is to use a correlated double sampler (CDS) 74 and a high-speed analog to digital converter (ADC) 76. In the embodiment shown, the sensor (an APD, PMT, or SiPM) 54, wide band transimpedance amplifier 62, and secondary amplifier 64 generally serve the same function as the components shown in FIG. 3. The primary difference however is that the correlated double sampler 74 removes undesired offsets from the signal; for example, the correlated double sampler 74 allows the subtraction of any offset generated due to output offset voltage of the amplifiers and reduces dark current noise components.

The correlated double sampler 74 initially triggers a first value from a charge signal of the kill laser based on a timer that starts when the cell is detected. Then, after a software-controlled charge delay and the kill laser 48 fires, the correlated double sampler 74 measures a second value and returns the subtracted value. The correlated double sampler 74 essentially produces the value:

$$VCDS=VSIGNAL-VDARK,$$

where VDARK represents the voltage measured from the sensor signal chain when a kill pulse is not fired, and VSIGNAL is the fluorescence measurement taken from the cell following a successful kill hit.

The high-speed analog to digital converter 76 is synced to the correlated double sampler 74 in the present implementation. When the correlated double sampler value is ready, the high-speed analog to digital converter 76 will sample the correlated double sampler output. The moment the high-speed analog to digital converter 76 samples are determined by the conversion time of the correlated double sampler 74 and the initial charge signal starts the correlated double sampler conversion clock, the high-speed analog to digital converter 76 value would be read in by the digital electronics 68, such as a field programmable gate array, and sent to either the embedded system or instrument personal computer.

Figure 7:
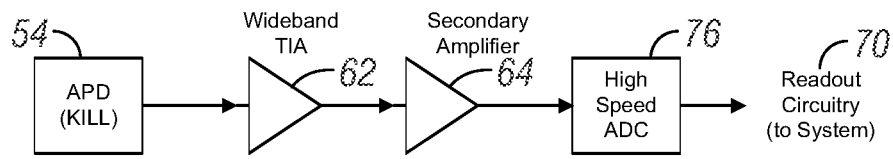
FIG. 7 shows a diagram of a third option for the kill acquisition electronics used in the sexed semen system of FIG. 2 for kill confirmation which includes a high-speed analog to digital converter according to some aspects of the present disclosure.

As shown in FIG. 7, another embodiment of the present disclosure utilizes a separate kill sensor (and APD, PMT, or SiPM) 54, wide band transimpedance amplifier 62, and secondary amplifier 64 as described in the previous sections. However, for the present implementation, a high-speed analog to digital converter 76 is used to simply digitize the pulse data and send the information upstream. A sample rate of 1 giga sample per second is a reasonable sample rate to obtain ten to sixteen data points per pulse. A high-speed field programmable gate array may be required for the present implementation to read the data from the analog to digital converter 76 and to send the information to the instrument embedded electronics or system personal computer.

Figure 8:
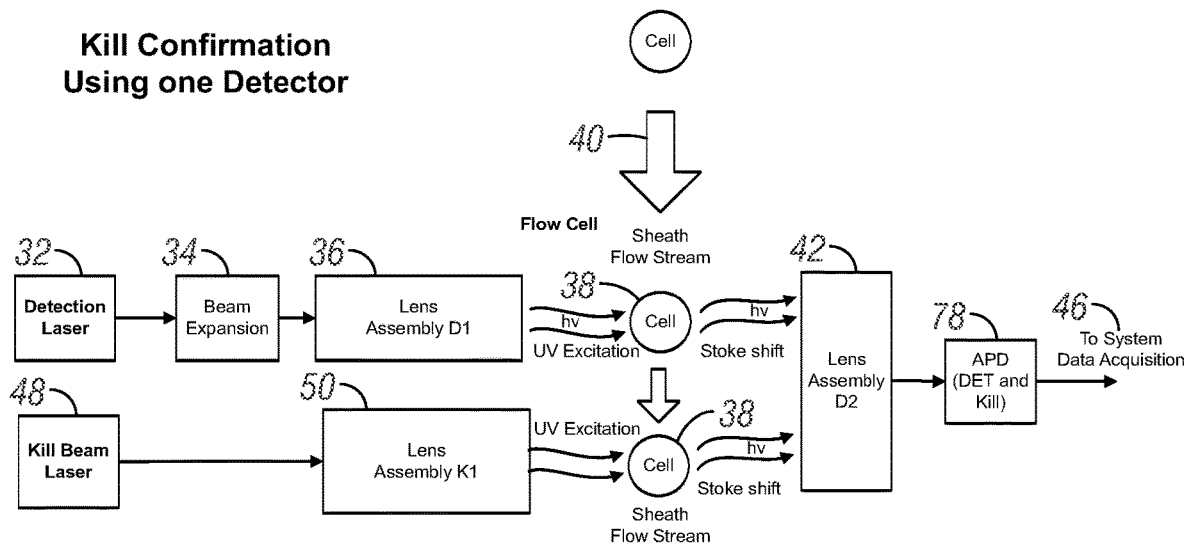
FIG. 8 shows a diagram of the sexed semen system implementation wherein a single detector is used for detection and kill in the instrument according to some aspects of the present disclosure.

FIG. 8 shows a possible kill confirmation using a single detector for detection and kill 78. The detection laser 32, kill laser 48, beam expansion 34, first detection laser lens assembly 36, and first kill laser lens assembly 50 perform identical functions as described previously for FIG. 2. In a preferred embodiment, the single detector for detection and kill 78 may be an avalanche photodiode sensor or a silicon photomultiplier.

To perform kill confirmation with a single detector 78, the second detection laser lens assembly 42 steers both the kill and the detection beam signals onto the same detector surface. The kill beam fluorescence in the present implementation is attenuated to avoid railing the detection amplifier when a kill beam pulse occurs.

Figure 9:
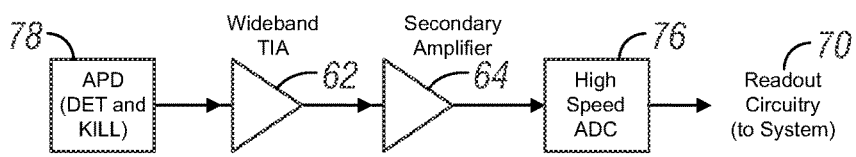
FIG. 9 shows a diagram of a first option for the kill acquisition electronics used in the sexed semen system of FIG. 8 for kill confirmation which includes a sample amplifier chain and high-speed analog to digital converter according to some aspects of the present disclosure.

FIG. 9 shows a possible implementation using a wide band transimpedance amplifier 62 and a secondary amplifier 64 to extend bandwidth. The kill pulse is approximately 200 times narrower than the detection pulse and therefore the wide band transimpedance amplifier 62 is needed to allow both signals to pass. The high-speed analog to digital converter 76 may be a flash or pipelined successive approximation (SAR) analog to digital converter operating in the giga sample range. The sample rate is required to obtain pulse information for the narrow pulse of the kill beam, as the architecture (flash/SAR) allows for acceptable conversion latency delay. The system averages samples for the detection pulse to reduce the noise and implements over-sampling noise reduction methods to aid in detection pulse noise performance. The kill signal is the raw waveform acquisition and digital signal processing techniques may be used to remove the kill signal from the waveform.

Figure 10:
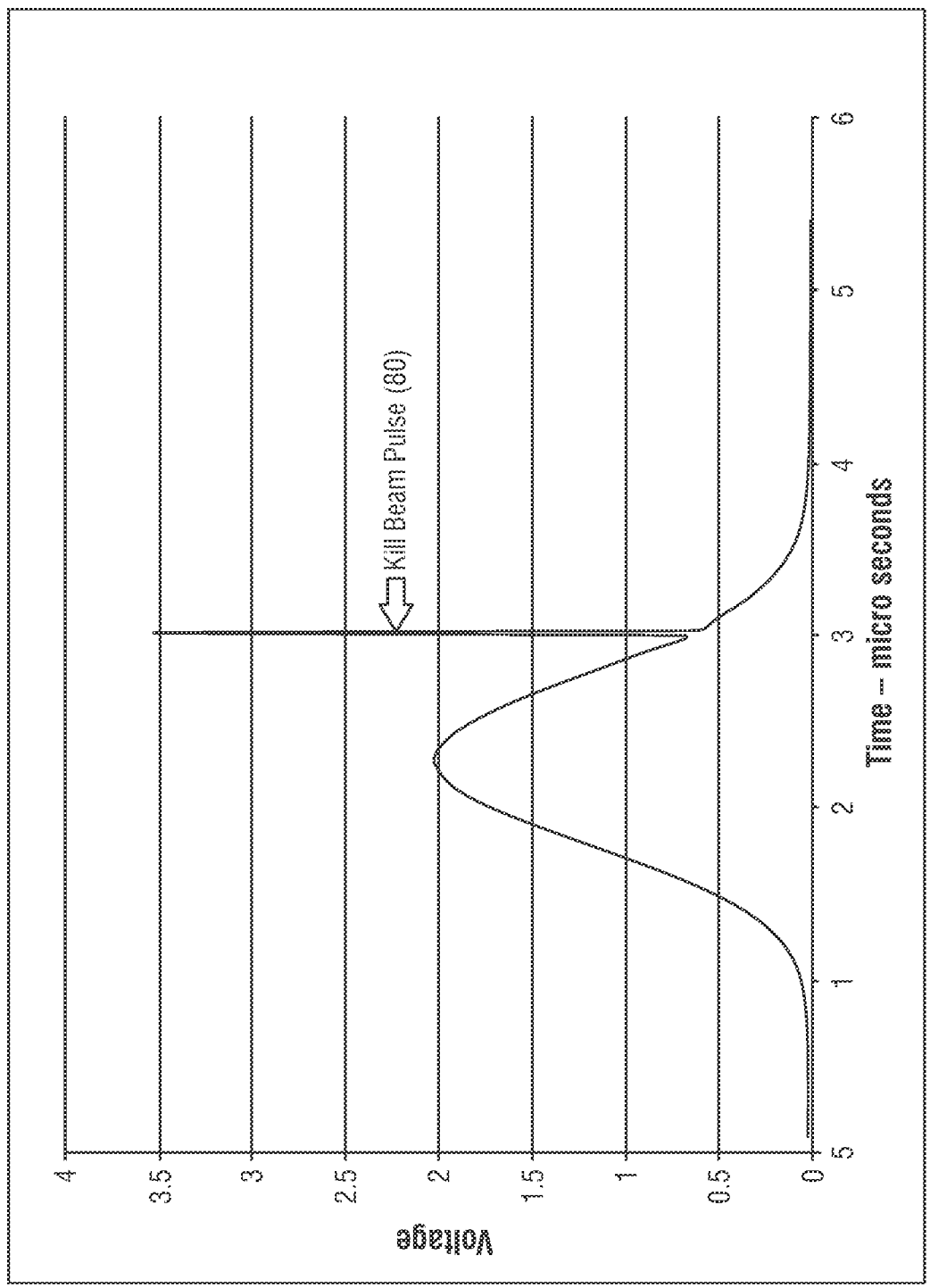
FIG. 10 shows a graphical representation of a detection pulse and a kill beam pulse according to some aspects of the present disclosure.

According to a non-limiting example of the present disclosure, a detection and kill beam pulse are shown in FIG. 10 wherein a kill beam pulse 80 overlaps a detection. After the signal digitization, the original detection pulse and kill beam pulse 80 are decoupled and reconstructed digitally as separate pulses.

Note the bandwidth required to achieve this acquisition is difficult with current analog electronics components. The gain required for the detection signal likely creates filtering that will not allow the kill beam pulse to pass. While this leaves the option to reduce the circuit gain, the noise floor of the system may be too high to resolve the cell populations. Thus, a combination of methods may be more suitable for the single detector solution wherein the analog signal is split between the detection and the high-speed acquisition methods mentioned in previous sections.

Figure 11:
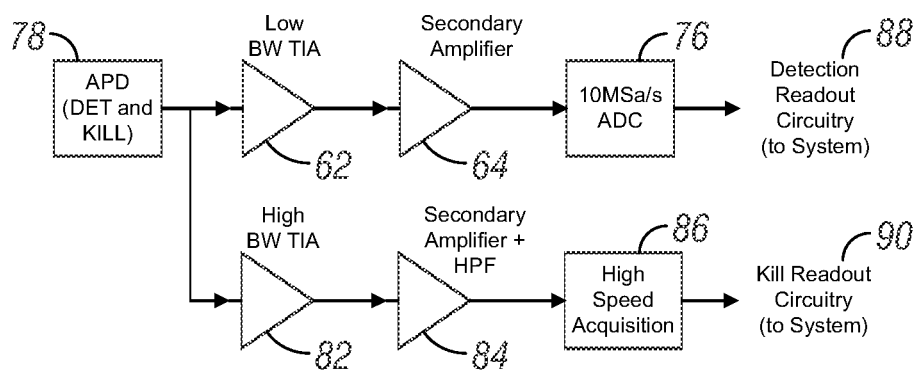
FIG. 11 shows a diagram of a second option for the kill acquisition electronics used in the sexed semen system of FIG. 8 for kill confirmation which includes an analog signal split for the single detector according to some aspects of the present disclosure.

FIG. 11 shows a potential solution that taps the current signal from the single detector for detection and kill 78 into two separate circuits, one for the low bandwidth detection (which includes an identical low bandwidth transimpedance amplifier 62 and secondary amplifier 64 used by the previously disclosed circuits) which is operatively connected to detection readout circuitry 88 of the system and the other for the high bandwidth kill beam signal which is operatively connected to kill readout circuitry 90 of the system.

The circuitry for the high bandwidth kill beam signal amplifies the high bandwidth signal from the kill laser cell fluorescence with a high bandwidth transimpedance amplifier 82. The combination secondary amplifier and high pass filter (HPF) 84 rejects any direct current (DC) component generated from the detection pulse and has a frequency stop band placed to reject as much of the detection signal as possible. Because the detection signal is much lower than the kill beam pulse, it may be possible to park the detection signal well below the kill beam confirmation high-speed acquisition 86 event threshold.

The microfluids subsystem of the sexed semen system mentioned above comprises a mass flow controller 91 which includes a microfluidic chip 92 having two sheath inlets 93, a sample inlet 94, two waste outlets 95, and a sample outlet 96; sheath outlets; a sheath tube 97; a sheath supply 98; and controller bleed ports 99. The mass flow controller 91 utilizes differential pressure-based flow metering, and the controller bleed ports 99 are capable of cleaning, flushing, or removing air from the sexed semen system.

According to additional aspects of the present disclosure, the sexed semen system may also include additional electrical components such as an intelligent control and communication components. Examples of such intelligent control units may be tablets, telephones, handheld devices, laptops, user displays, or generally any other computing device capable of allowing input, providing options, and showing output of electronic functions. Still further examples include a microprocessor, a microcontroller, or another suitable programmable device) and a memory. The apparatus also can include other components and can be implemented partially or entirely on a semiconductor (e.g., a field-programmable gate array ("FPGA")) chip, such as a chip developed through a register transfer level ("RTL") design process. The memory includes, in some embodiments, a program storage area and a data storage area. The program storage area and the data storage area can include combinations of different types of memory, such as read-only memory ("ROM"), random access memory ("RAM") (e.g., dynamic RAM ("DRAM"), synchronous DRAM ("SDRAM"), etc.), electrically erasable programmable read-only memory ("EEPROM"), flash memory, a hard disk, an SD card, or other suitable magnetic, optical, physical, or electronic memory devices.

A communications module can be included with the sexed semen system and can be configured to connect to and communicate with a controller, such as a computer, tablet, server, or other computing device. This could allow the sexed semen system to provide data or other information (e.g., warnings, status, notices, etc.) associated with the sexed semen system to a remote location of the controller to allow the real-time information and stored information for the sexed semen system. The information could be used to determine issues, forecast, or otherwise track information related to the sexed semen system. The communication could also be in the form of inputs such that the communication could include a command to the sexed semen system from a remote location.

In some embodiments, the sexed semen system includes a first communications module for communicating with a secondary device (another sexed semen system or remote controller), and/or a second communications module for communicating with a central location (server, computer, or other master controller). For sake of simplicity, the term "communications module" herein applies to one or more communications modules individually or collectively operable to communicate with both the sexed semen system and the central location.

The communications module communicates with the central location through the network. In some embodiments, the network is, by way of example only, a wide area network ("WAN") (e.g., a global positioning system ("GPS"), a TCP/IP based network, a cellular network, such as, for example, a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a Digital Enhanced Cordless Telecommunications ("DECT") network, a Digital AMPS ("IS-136/TDMA") network, or an Integrated Digital Enhanced Network ("iDEN") network, etc.), although other network types are possible and contemplated herein. In certain embodiments, the network is a GSM or other WAM which is operable to allow communication between the communications module and the central location during moments of low-quality connections, such as but not limited to when the sexed semen system is near a window.

The network can be a local area network ("LAN"), a neighborhood area network ("NAN"), a home area network ("HAN"), or personal area network ("PAN") employing any of a variety of communications protocols, such as Wi-Fi, Bluetooth, ZigBee, near field communication ("NFC"), etc., although other types of networks are possible and are contemplated herein. Communications through the network by the communications module or the controller can be protected using one or more encryption techniques, such as those techniques provided in the IEEE 802.1 standard for port-based network security, pre-shared key, Extensible Authentication Protocol ("EAP"), Wired Equivalency Privacy ("WEP"), Temporal Key Integrity Protocol ("TKIP"), Wi-Fi Protected Access ("WPA"), and the like.

Finally, it is noted the present disclosure contemplates components of the sexed semen system may be powered in a number of ways. The components of the system can be hard-wired, cord and plug connected, or otherwise powered, such as to AC power plugs and sockets. A hardwired component is one where the building wiring method attaches to the component in a more permanent fashion. This will involve splicing of wires inside the component or in a junction box. Cord and plug connected components have a cord with a molded plug that is either factory or field installed on the component. The component is then ready to be plugged in to a receptacle in the location it is permanently installed. The hard-wired power source could be on a power grid, or could be a separate generator, battery, or other source. The wire could provide power over Ethernet or via USB cable, such as if the system is connected in such a manner. Still further, it is contemplated that the system be self-powered or include on-board power, in that there is no wiring to a separate power source. Such a configuration could include batteries in the system, such as non-rechargeable (e.g., dry battery) or rechargeable (e.g., Lithium-ion) type batteries. Still further, other types of power, such as, but not limited to, solar, piezoelectric sources, and the like, which can provide additional amounts of power.

In certain aspects, the detector systems described above can be used to verify and adjust the alignment of the sorting mechanism in the apparatus. In certain embodiments, the apparatus includes a kill (or ablation) laser that selectively kills or inactivates unwanted cells. The kill laser is typically of a wavelength that excites the fluorescent dye. When a cell is struck by the kill laser, the fluorescent dye inside the cell emits light which is then collected and measured by a detector (or any of the previously mentioned techniques). The measurement output from the detector is proportional of the intensity of the light emitted by the cell. The emission intensity of each cell is a characteristic of the DNA content, orientation, and location of the cell relative to the kill laser (i.e. the kill laser alignment with the fluid stream), and the excitation energy delivered to that cell.

Kill laser alignment with the fluid stream (as assessed by determining the cell location relative to the kill laser) is key to ensuring that targeted cells are effectively killed. Typically, the beam of the kill laser is elliptical, where the vertical axis parallel to the direction of flow is much smaller than the horizontal axis, with a gaussian intensity distribution. The intensity distribution is such that cells located at the center of the kill laser are effectively sliced while cells towards the edge of the laser may only be killed but not sliced. Further, cells located insufficiently close to the high intensity (center) area of the beam may receive a photon that is insufficient to incapacitate. Thus, it is desirable to ensure that cells are aligned to the center of the laser beam for optimal kill performance.

The following three conditions are generally true of sorting systems using such a kill laser: (1) The kill laser intensity is maximum at the center of the spot and decreases as you move away from the center in any direction; (2) the emission intensity of a cell struck by the kill laser is proportional to the laser intensity intersecting the cell, and (3) the emission intensity of a cell struck by the kill laser is proportional to the intensity measured at the detector. As a result, the detector intensity measurement can be used to assess whether and to what extent a cell has been struck by the kill laser, and therefore as a feedback mechanism to optimize the position of a cells relative to the center of the kill laser. With the majority of cells positioned at the center of the kill laser, the detector will measure maximum average intensity for a sample of cells (n>1). The input to the feedback system could be a stage positioning cells to a fixed kill laser location or a timing delay in the direction of flowing cells. In some aspects, a searching algorithm is implemented to find the maximum intensity position. If completed in a short enough time, this searching and find approach can be used to initially align an instrument for collection, as well as being used to maintain alignment during collection.

In some aspects, the secondary detection of fluorescence from cells exposed to the kill laser can further involve approaches to provide a more informative measure—enable more accurate comparison, allow for orientation determination, provide more sensitive feedback and adjustment. In certain aspect, the approaches may involve calculating the area of the signal through pulse-stretching and window comparison. In general, a modified electronics configuration would allow for the extraction of more characteristics of any individual pulse and in turn more characteristics of the kill event. Characteristics can include total energy delivered to the cell, and metrics for kill laser pulse length variation. The slope of the pulse may indicate how quickly the energy is delivered to the cell.

In other aspects, the secondary detection of fluorescence from cells exposed to the kill laser can be used to the secondary detection of fluorescence from cells exposed to the kill laser can be used to assess the orientation of the cells. Sperm cells are non-uniform in shape, have a long axis (head to tail), a wide axis, and a deep axis. It is understood that the ability to effectively discriminate between X- and Y-chromosome bearing sperm cells on the basis of a ~4% difference in DNA content requires that the cells be consistently oriented with respect to the detector—inconsistency in orientation can result in loss of the ability to resolve the two populations based on fluorescence intensity, and therefore loss of the ability to effectively discriminate and selectively target one of the populations for sexing. Maximum resolution in detection is achieved when the cells are consistently oriented such that the wideset axis of the cells is parallel to the face of the detector—that is, the flattest surface of the cell is perpendicular to the axis along which the detector is receiving the fluorescence signal. Variation in this orientation yields changes in the intensity of the signal that is detected. As a result, variation in the fluorescence intensity can be used to assess the orientation of the cells. Thus, in certain aspects, the secondary detector can be utilized for additional determination or confirmation of cell orientation.

LIST OF REFERENCE NUMERALS

The following reference numerals are provided to facilitate an understanding and examination of the present disclosure and are not an exhaustive list. Provided it is possible to do so, elements identified by a numeral may be replaced or used in combination with any elements identified by a separate numeral. Additionally, numerals are not limited to the descriptors provided herein and include equivalent structures and other objects possessing the same function

TABLE 1

| | List of Reference Numerals |
|---|---|
| 30 | improved semen sexing instrument or cytometer |
| 32 | detection laser |
| 34 | beam expansion |
| 36 | first detection laser lens assembly |
| 38 | flow cell |
| 40 | sample flow stream |
| 42 | second detection laser lens assembly |
| 44 | first detector/avalanche photodiode sensor/photomultiplier tube/silicon photomultiplier |
| 46 | system data acquisition |
| 48 | kill laser/kill beam |
| 50 | first kill laser lens assembly |
| 52 | second kill laser lens assembly |
| 54 | second detector/avalanche photodiode sensor/silicon photomultiplier/kill detector |
| 56 | kill acquisition electronics |
| 58 | system control interface |
| 60 | high voltage circuitry |
| 62 | wide band/low bandwidth transimpedance amplifier |
| 64 | secondary amplifier |
| 66 | high-speed comparator |
| 68 | digital circuitry/digital electronics |
| 70 | readout circuitry |
| 72 | comparator/resistor ladder configuration |
| 74 | correlated double sampler |
| 76 | high-speed analog to digital converter |
| 78 | single detector for detection and kill |
| 80 | kill beam pulse |
| 82 | high bandwidth transimpedance amplifier |
| 84 | combination secondary amplifier and high pass filter |
| 86 | high-speed acquisition |
| 88 | detection readout circuitry |
| 90 | kill readout circuitry |
| 91 | mass flow controller |
| 92 | microfluidic chip |
| 93 | sheath inlets |
| 94 | sample inlet |
| 95 | waste outlets |
| 96 | sample outlet |
| 97 | a sheath tube |
| 98 | a sheath supply |
| 99 | controller bleed ports |
| 100 | cell kill confirmation method |
| 101 | flowing step |
| 102 | exciting step |
| 103 | first measuring step |
| 104 | classifying step |

TABLE 1-continued

List of Reference Numerals

| | |
|---|---|
| 105 | determining step |
| 106 | queuing step |
| 107 | firing step |
| 108 | second measuring step/providing step |
| 109 | collecting step |

The disclosure is not to be limited to the particular embodiments described herein. The previous detailed description is of a small number of embodiments for implementing the disclosure and is not intended to be limiting in scope. The following claims set forth a number of the embodiments of the disclosure with greater particularity.

The invention claimed is:

1. A method for producing a sexed semen sample, the method comprising:
   illuminating a cell with a focused beam of electromagnetic radiation;
   detecting a first fluorescence by the cell;
   determining a set of characteristics of the cell based on the fluorescence of the cell;
   identifying the cell as an undesired cell based on the set of characteristics;
   setting a timing signal for a kill laser wherein the timing signal causes the kill laser to emit a focused beam of electromagnetic radiation at the cell;
   firing the kill laser at the cell based on the timing signal;
   detecting a second fluorescence by the cell;
   determining a type of event based on the second fluorescence, wherein the type of event is one of a slice, a kill, or a miss.

2. The method of claim 1, further comprising aligning the kill laser prior to firing, wherein the alignment ensures that the emitted focused beam from the kill laser accurately targets the identified undesired cell.

3. The method of claim 1, wherein output is provided to a user indicating whether the type of event is one of a slice, a kill, or a miss.

4. The method of claim 1, wherein the timing signal for the kill laser is set based on a real-time analysis algorithm that dynamically adjusts the timing to optimize the type of event as a kill.

5. The method of claim 1, further comprising storing the data related to the second fluorescence and the type of event in a database for quality control and analysis.

6. The method of claim 1, wherein output is provided to the user indicating results from multiple events, including but not limited to the aggregate or average number of the types of events.

7. The method of claim 1, wherein the detection and the kill laser use the same wavelength and allow for determining the type of event is one of a kill using only one dye.

8. The method of claim 1, wherein the kill laser uses ultraviolet or infrared irradiation, and the type of event is one of a kill.

9. The method of claim 1, further comprising exciting the cell with a detection laser or a light emitting diode to cause the first fluorescence.

10. The method of claim 9, further comprising aligning the detection laser and wherein the detection laser utilizes beam conditioning to aid in achieving a correct spot size at the cell.

11. The method of claim 1, further comprising collecting the cell if the cell is identified as a desired cell based on the set of characteristics.

12. The method of claim 1, further comprising a sheath fluid encapsulating the cell.

13. The method of claim 1, wherein inertial flow focusing is utilized.

14. The method of claim 1, further comprising kill acquisition electronics including at least a wide band transimpedance amplifier operatively connected to the second fluorescence detector.

15. A method for determining the orientation of a particle, the method comprising:
   illuminating a particle with a focused beam of electromagnetic radiation;
   detecting a first fluorescence by the particle;
   identifying the particle as one of a first type or one of a second type;
   measuring a second fluorescence by the particle;
   identifying the particle as one of a first type or one of a second type based on the second fluorescence;
   determining the orientation of the particle based on the first and second fluorescence, and providing output to the user on the orientation.

16. The method of claim 15, wherein output is provided to the user indicating orientation of multiple particles, including but not limited to the aggregate or average number of the orientations of the particles.

* * * * *